US006393915B1

(12) United States Patent
Banet et al.

(10) Patent No.: US 6,393,915 B1
(45) Date of Patent: May 28, 2002

(54) METHOD AND DEVICE FOR SIMULTANEOUSLY MEASURING MULTIPLE PROPERTIES OF MULTILAYER FILMS (75) Inventors: Matthew John Banet, Boston; Robin Anne Sacco, Franklin, both of MA (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 0 days.

(21) Appl. No.: 09/363,350

(22) Filed: Jul. 29, 1999

(51) Int. Cl.[7] .............................. G01H 9/00; G01B 11/02
(52) U.S. Cl. ............................. 73/579; 73/599; 73/643; 73/655; 356/503
(58) Field of Search ......................... 73/579, 643, 597, 73/599, 655; 356/432, 445, 450, 496, 498, 502, 503

(56) References Cited

U.S. PATENT DOCUMENTS

| | | | |
|---|---|---|---|
| 4,679,946 A | * 7/1987 | Rosencwaig et al. | 374/5 |
| 5,546,811 A | 8/1996 | Rogers et al. | 73/800 |
| 5,633,711 A | * 5/1997 | Nelson et al. | 356/318 |
| 5,672,830 A | * 9/1997 | Rogers et al. | 73/597 |
| 5,734,540 A | 3/1998 | Jacobs et al. | 360/132 |
| 5,748,318 A | * 5/1998 | Maris et al. | 356/381 |
| 5,812,261 A | 9/1998 | Nelson et al. | 356/318 |
| 6,016,202 A | * 1/2000 | Fuchs et al. | 356/432 T |
| 6,052,185 A | * 4/2000 | Banet et al. | 356/345 |
| 6,069,703 A | * 5/2000 | Banet et al. | 356/432 |
| 6,081,330 A | * 6/2000 | Nelson et al. | 356/318 |

* cited by examiner

Primary Examiner—Richard A. Moller (57) ABSTRACT

The invention relates to a method and device for simultaneously measuring multiple properties of a sample composed of multiple layers of films. The measurement features several steps. First, at least one source of excitation radiation irradiates the sample's surface to excite an acoustic mode. A probe source of radiation irradiates the acoustic mode and is diffracted off the surface of the sample to form a signal beam. A detector detects the acoustic mode to generate a signal beam, which is then analyzed to determine an acoustic frequency and an amplitude, a depth of modulation, or a decay constant. These properties are then further analyzed to determine of at least two properties (e.g., a thickness of two layers) of the sample.

15 Claims, 10 Drawing Sheets

Fig. 1

Fig. 2B  TiN on Aluminum

Fig. 2A  TiN on Oxide

Fig. 3

Ti:Nitride Thickness - Sheet Resistance

Fig. 4B

Ti:Nitride Thickness - ISTS

Fig. 10

METHOD AND DEVICE FOR SIMULTANEOUSLY MEASURING MULTIPLE PROPERTIES OF MULTILAYER FILMS

FIELD

This invention relates to a method and apparatus for measuring material properties of multiple layers of films (e.g., the thicknesses of thin films) contained in a multi-layer sample.

BACKGROUND

Thin films of dielectric (e.g., polymer, oxide) and conducting (e.g., metal) materials are used in a range of microelectronic, optical, and biomedical devices. A microprocessor, for example, contains multiple layers of metal and oxide thin films deposited on a semiconducting material. Thickness variations in these films can modify the films' electrical and mechanical properties, thereby affecting the performance of the microprocessor. Accordingly, film thickness is often monitored as a quality-control parameter during and/or after the microprocessor's fabrication.

Several film measurement techniques, such as optical ellipsometry, reflectometry, and Impulsive Stimulated Thermal Scattering (ISTS), have been previously developed to measure oxide and metal films during fabrication of a microprocessor.

Ellipsometry is a well-known optical technique that measures the change in polarization of a light beam after it has irradiated a film. It is typically used to measure the thickness and complex refractive index of transparent (e.g., oxide, nitride) films disposed on the surface of a silicon wafer. Reflectometry is a similar optical technique that measures the change in intensity of a light beam after it has reflected off the surface of a film. Similar to ellipsometry, reflectometry measures the thickness of transparent films disposed on the surface of a silicon wafer.

ISTS is an optical technique that measures the thickness of thin metal films. It is described, for example, in pending and issued U.S. Pat. No. 5,633,711 (entitled MEASUREMENT OF MATERIAL PROPERTIES WITH OPTICALLY INDUCED PHONONS); U.S. Pat. No. 5,546,811 (entitled OPTICAL MEASUREMENT OF STRESS IN THIN FILM SAMPLES); and U.S. Pat. No. 5,812,261 (entitled METHOD AND DEVICE FOR MEASURING THE THICKNESS OF OPAQUE AND TRANSPARENT FILMS), the contents of which are incorporated herein by reference. In ISTS, a first laser pulse initiates a sound wave that propagates in a plane of the film. A second laser pulse measures a frequency of the sound wave. The frequency of the sound wave relates to film thickness.

A typical ISTS measurement determines the thickness of a single film in a multilayer stack of thin films. There exists a need, however, to measure the thickness of multiple layers in the stack of films.

SUMMARY

In response to industry demand, the invention provides a method and apparatus for simultaneously measuring multiple properties (e.g., multiple thicknesses) of a sample composed of multiple layers of films.

In general, in one aspect, the invention provides a method for measuring properties of a sample with multiple layers of films. The method involves three basic steps: 1) irradiating a surface of the sample with at least one source of excitation radiation to excite an acoustic mode within the sample; 2) detecting the acoustic mode with a probe source of radiation which generates a signal beam that has both an oscillating component and a second, time-dependent component; and 3) analyzing a frequency of the oscillating component and analyzing at least an amplitude of the second time-dependent component, a depth of modulation of the oscillating component, or a decay constant of the second time-dependent component of the signal beam to determine at least two properties of the sample.

In one embodiment, the analysis step determines at least one property of the sample (e.g., the thickness of one layer) from the frequency of the oscillating component. At least one additional property of the sample (e.g., the thickness of a second layer) is determined from either the amplitude of the second time-dependent component, the depth of modulation of the oscillation component, or the decay constant of the second time-dependent component of the signal beam. For example, in one embodiment, one of these components is compared to a mathematical model to determine a thickness value. The mathematical model contains either an exponential component or a sinusoidal component that is used to model at least one property of the sample. This property can be the thickness of an outer film in a multilayer film structure.

In another aspect, the invention provides an apparatus for measuring a sample that includes: 1) at least one source of excitation radiation that initiates a response in a sample; 2) at least one source of probe radiation that irradiates the response to generate a signal beam that has an oscillation component and a second, time-dependent component; 3) a detector for detecting the signal beam to generate a light-induced electrical signal; and 4) an analyzer that analyzes the light-induced electrical signal to determine at least two properties of the sample from the frequency of the oscillation component and from at least the amplitude of the second time-dependent component, the depth of modulation of the oscillation component, or the decay constant of the second time-dependent component of the signal beam.

In another aspect, the invention provides an alternative method for measuring properties of a multilayer sample. This method includes: 1) irradiating a surface of the sample with a first source of excitation radiation to excite an acoustic mode within the sample; 2) detecting the acoustic mode with a probe source of radiation to generate a first signal beam; 3) irradiating a surface of the sample with a second source of radiation to generate a second signal beam; and 4) analyzing the first and second signal beams to determine at least two properties of the sample.

In one embodiment, the second probe source of radiation reflects off of the sample to generate the second signal beam. In further embodiments, the second signal beam differs from the second probe source of radiation in intensity, polarization, or a combination of intensity and polarization. This change in intensity, polarization, or combination of intensity and polarization is compared to a mathematical model to determine at least one property (e.g., thickness) of the outermost layer of the sample. The analyzer (e.g., a computer or microprocessor) determines a change in intensity between the second source of excitation radiation and the reflected second signal beam. In further embodiments, the analyzer compares the change in intensity between the second source of excitation radiation and the reflected second signal beam to a mathematical model to determine a property (i.e., thickness) of the outermost layer of the sample.

In another embodiment, the analyzer measures a change in polarization between the second source of excitation radiation and the reflected second signal beam. The analyzer compares this change in polarization to a mathematical model to determine a property (i.e., thickness) of the outermost layer of the sample.

The invention has many advantages. In general, the invention involves an all-optical, non-contact measurement technique that simultaneously and effectively measures both the thickness of thin surface films and properties (i.e., thickness, density, etc.) of underlying films, all of which are contained in a multi-layer structure. The thickness and property values can then be used to control a fabrication process (e.g., fabrication of a microelectronic device).

In the primary embodiment, unexpected functional advantages arise from determining multiple film thickness values from both the acoustic frequency and at least one of the amplitude, depth of modulation, or decay constant of the signal beam. Since each of these properties is derived from the same signal beam, both surface films and underlying layers are measured quickly and simultaneously with a single apparatus.

The apparatus features all the advantages of optical metrology: each measurement is non-contact, remote (the optical system can be as far as 10 cm or more from the sample), and can be made over a small region (as small as about 20 microns). Other properties besides film thickness may also be measured more precisely through the use of the invention.

Other features, aspects, and advantages of the invention follow from the following detailed description, and from the claims.

DETAILED DESCRIPTION

Method for Measuring the Thickness of Multiple Thin Films

Figure 1:
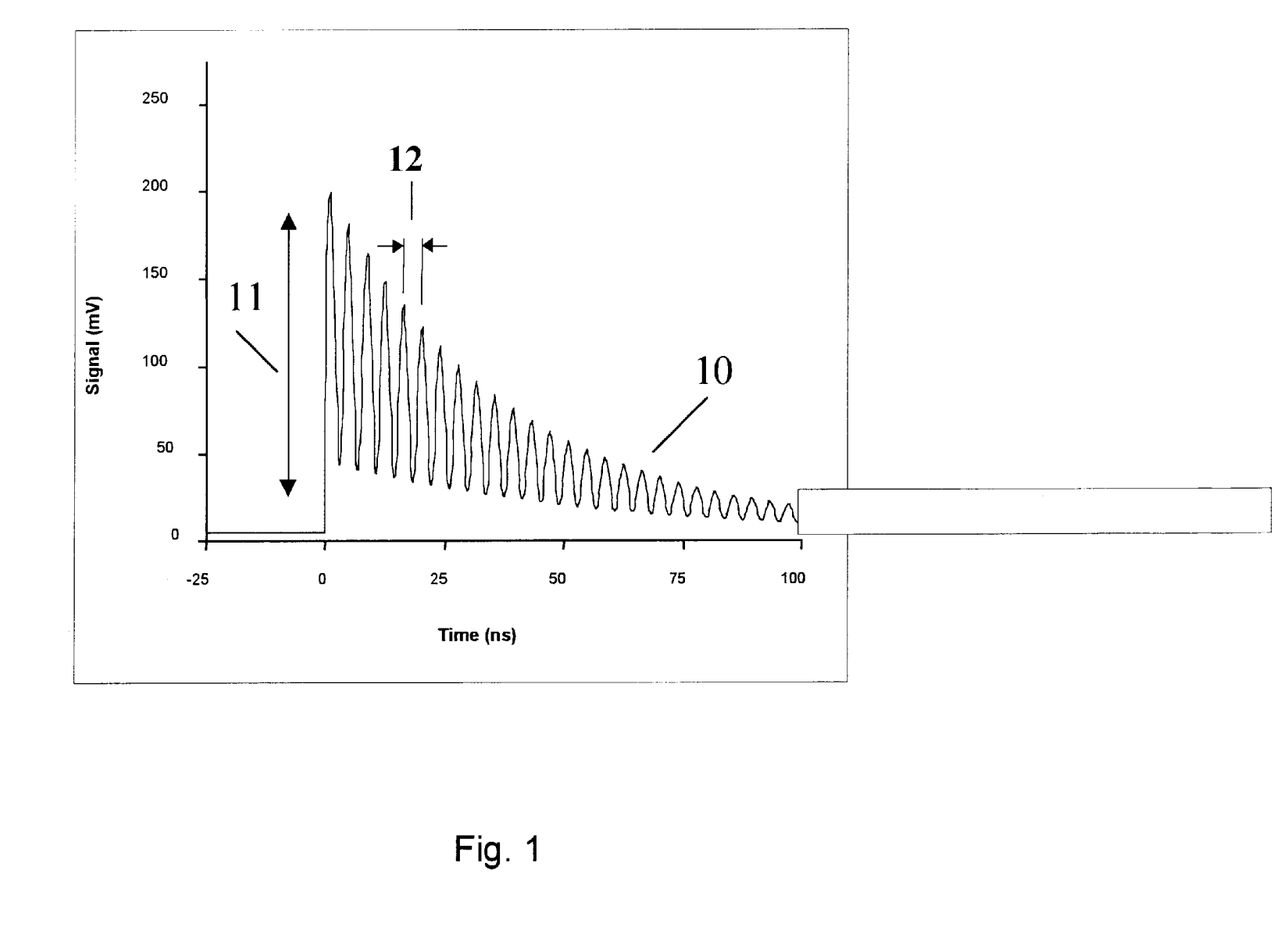
FIG. 1 is a graph of a signal waveform featuring an acoustic frequency and a signal amplitude.

Referring to FIG. 1, a signal waveform 10, measured using Impulse Stimulated Thermal Scattering (ISTS) from a ti:nitride film deposited on an aluminum film, features time-dependent properties such as amplitude 11 and acoustic frequency 12. The ISTS method used to generate the signal waveform 10 is described, for example, in pending and issued U.S. Pat. No. 5,633,711 (entitled MEASUREMENT OF MATERIAL PROPERTIES WITH OPTICALLY INDUCED PHONONS), U.S. Pat. No. 5,734,540 (entitled DEVICE AND METHOD FOR TIME-RESOLVED OPTICAL MEASUREMENTS), and U.S. Pat. No. 5,546,811 (entitled OPTICAL MEASUREMENT OF STRESS IN THIN FILM SAMPLES), the contents of which are previously incorporated by reference. The acoustic frequency 12 of the signal waveform 10 can be analyzed to determine the aluminum film thickness. This analysis process is described, for example, in pending and issued U.S. Pat. No. 5,812,261 (entitled METHOD AND DEVICE FOR MEASURING THE THICKNESS OF OPAQUE AND TRANSPARENT FILMS), the contents of which are incorporated herein by reference.

Figure 5:
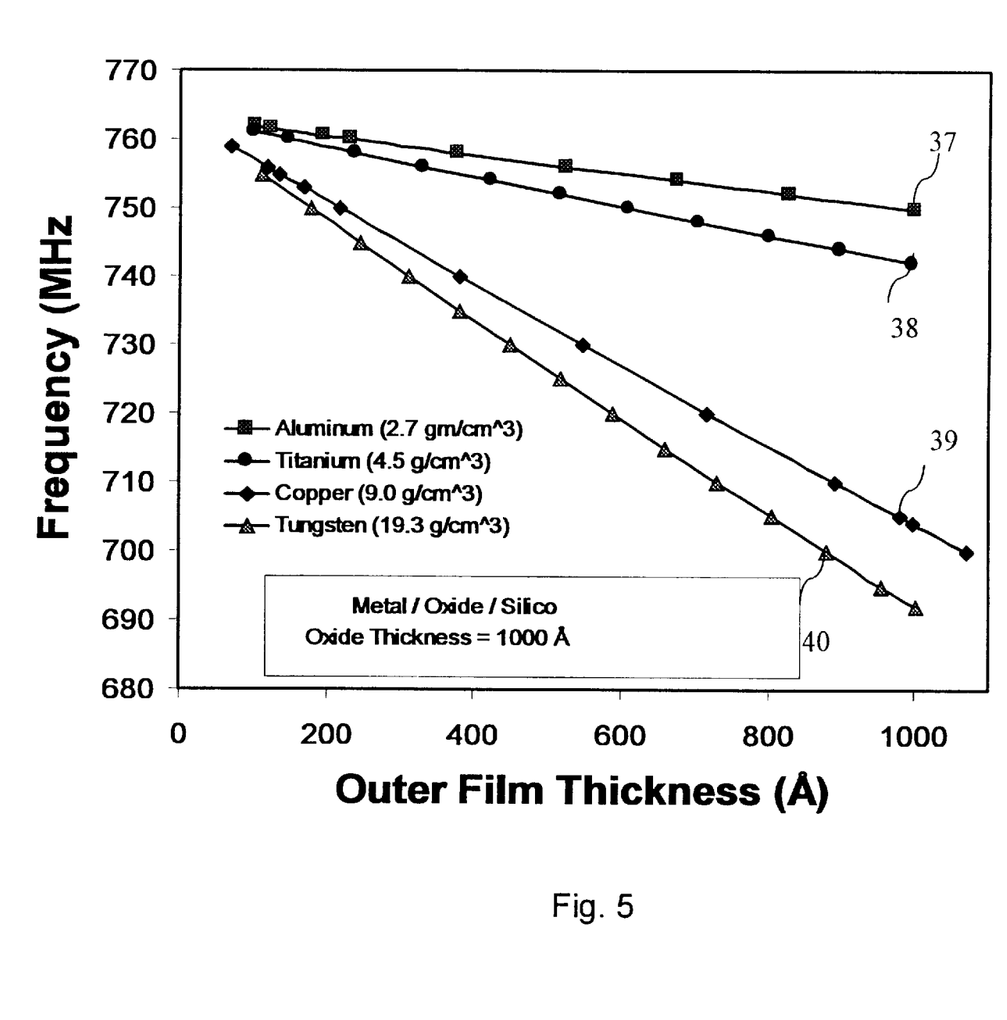
FIG. 5 is a graph of acoustic frequency versus film thickness for several thin-film materials.

FIG. 5, for example, shows how acoustic frequency (plotted along the y axis) corresponds to film thickness (plotted along the x axis) for several different materials. As indicated by the data points 37, 38, 39, 40 in the figure, the dependence of acoustic frequency on film thickness is nearly linear for metals such as aluminum, titanium, copper, and tungsten. As the film thickness increases, the frequency of the signal waveform decreases. The slope of the data points 37, 38, 39, 40 becomes steeper as the density of the metal increases.

It was recently and unexpectedly discovered that the amplitude 11 of the signal waveform 10 corresponds to the thickness of the overlying ti:nitride film. Thus, more than one property of a multilayer film stack can be measured using a single signal waveform 10.

Figure 2A:
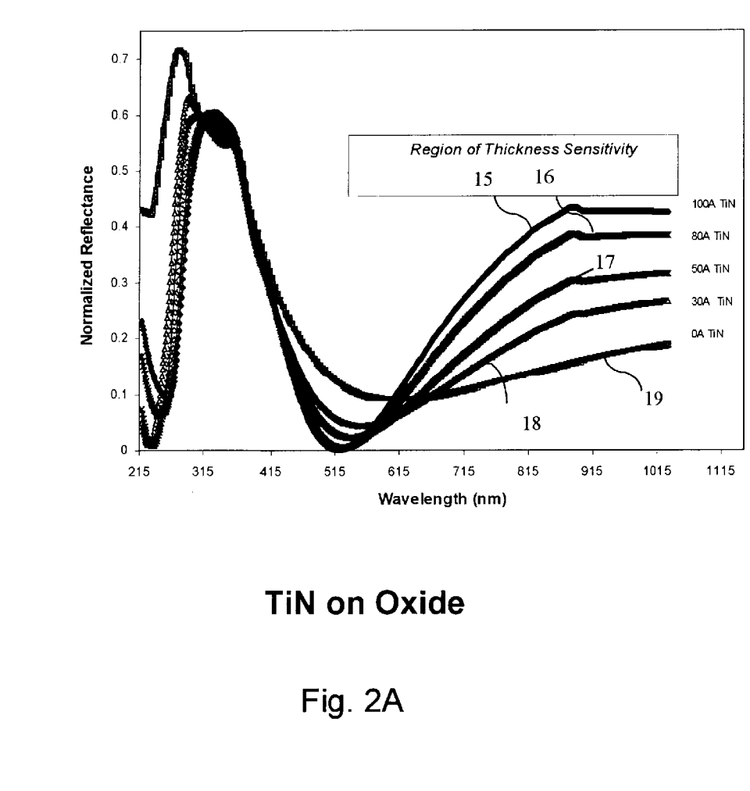
FIGS. 2A and 2B are, respectively, graphs depicting normalized reflectance versus wavelength for different thicknesses of a ti:nitride film deposited on a 1000-angstrom oxide film and 5000-angstrom alumninum film.
Figure 2B:
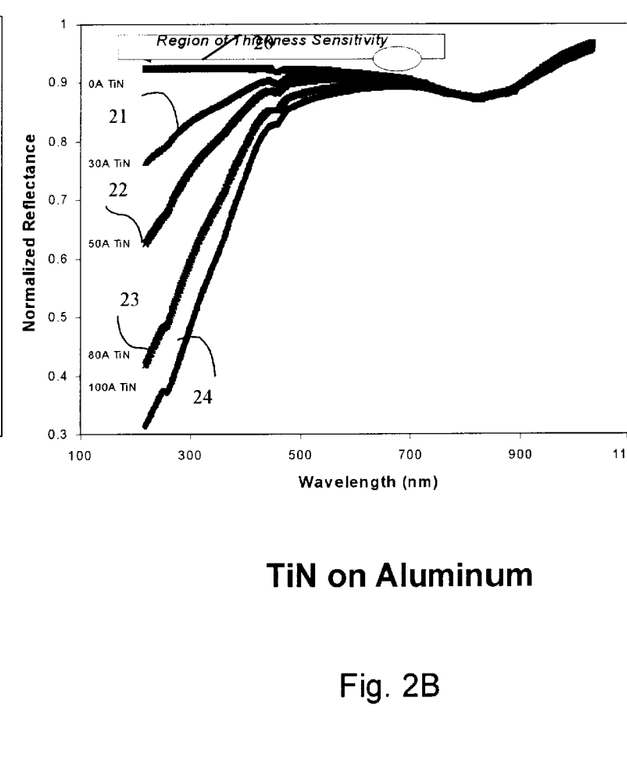

FIGS. 2A and 2B show how the amplitude of an ISTS-generated signal waveform, such as that shown in FIG. 1, varies with film thickness. These graphs show, respectively, optical reflectivity of a series of films (15–19 in FIG. 2A; 20–24 in FIG. 2B) having different thickness as a function of optical wavelength. FIGS. 2A and 2B show, respectively, graphs of optical reflectivity for ti:nitride films ranging from 0 to 100 A on oxide and aluminum. In FIG. 2A, film reflectivity varies strongly with ti:nitride thickness at wavelengths above about 700 nm, while reflectivity is relatively independent of film thickness at wavelengths below 400 nm. Conversely, FIG. 2B shows that for ti:nitride films on aluminum, optical reflectivity depends strongly on ti:nitride thickness at wavelengths less than 500 nm, but is independent of ti:nitride thickness at wavelengths larger than 830 nm.

The reflectivity properties of ti:nitride films FIGS. 2A and 2B indicate that during an ISTS measurement the optical reflectivity of the excitation beams depends on their wavelength and the thickness of the outer ti:nitride film. This means that the optical absorption of these beams, and hence the amplitude of the signal waveform, depends on the thickness of the ti:nitride film. For example, when a structure featuring ti:nitride on aluminum is measured with an excitation wavelength of about 500 nm, the amount of reflected light increases with decreasing ti:nitride film thickness. This, in turn, means the absorption of the excitation wavelength will increase for thicker films. An increase in optical absorption increases the signal magnitude of the ISTS signal. In this way, a correlation database (e.g., a table of numbers) relating ISTS signal magnitude and ti:nitride thickness can be determined. Once this correlation is determined, a measurement can be performed on an additional ti:nitride film. The amplitude of the signal waveform measured from this film is determined and then compared to the correlation database to determine the ti:nitride film thickness.

Figure 3:
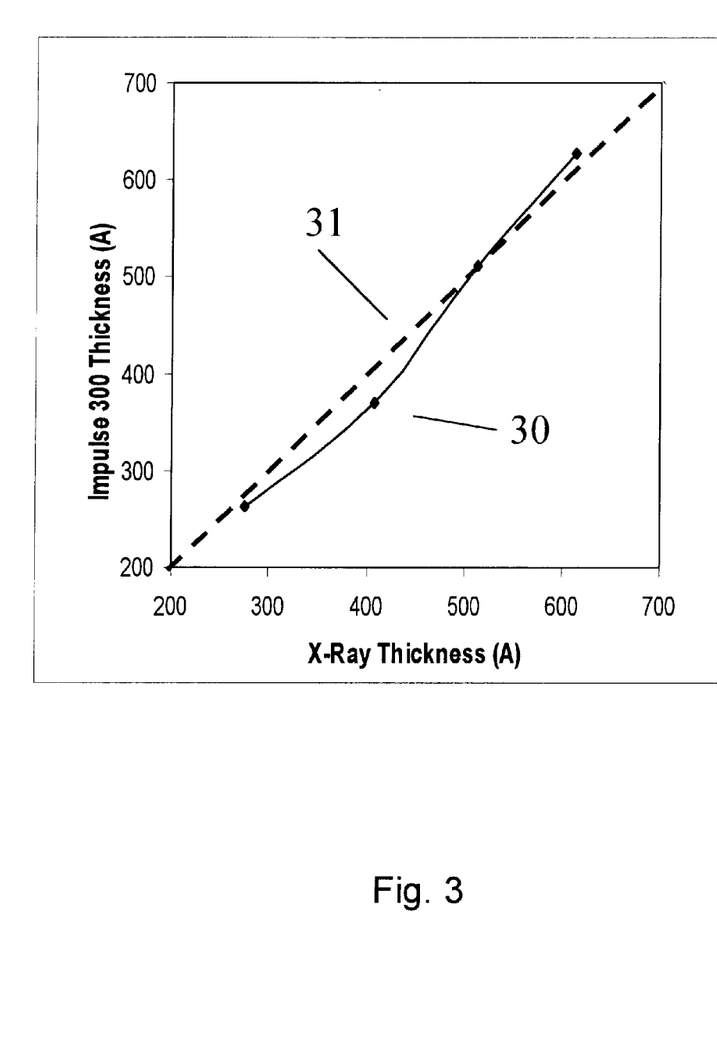
FIG. 3 is a graph of thickness of a ti:nitride film as measured by analyzing the amplitude of a signal waveform determined with ISTS versus the thickness of the ti:nitride film as measured using X-ray fluorescence.

FIG. 3 shows the correlation between ti:nitride thickness determined using the above-mentioned method (shown as the Y axis) and X-Ray fluorescence (shown as the X axis). X-Ray fluorescence is known to be a reliable method for measuring film thickness. In the figure, the curve 30 is drawn through data points that indicate ti:nitride films measured with the two techniques. A dashed straight line 31 with a slope of 1 is drawn in the figure to show the correlation. The similarity between the curve 30 and the straight line 31 indicates that the above-mentioned ISTS method and X-Ray fluorescence determine approximately the same thickness of a range of thin ti:nitride films.

Figure 4A:
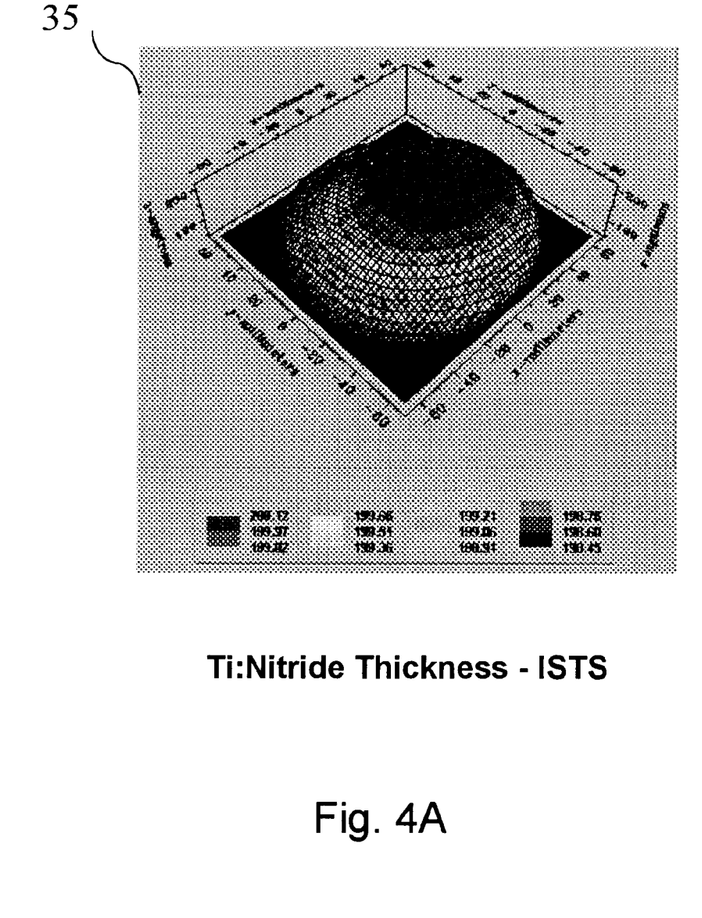
FIGS. 4A and 4B are, respectively, thickness contour maps of a surface ti:nitride film measured by analyzing the amplitude determined using ISTS and a 4-point probe.
Figure 4B:
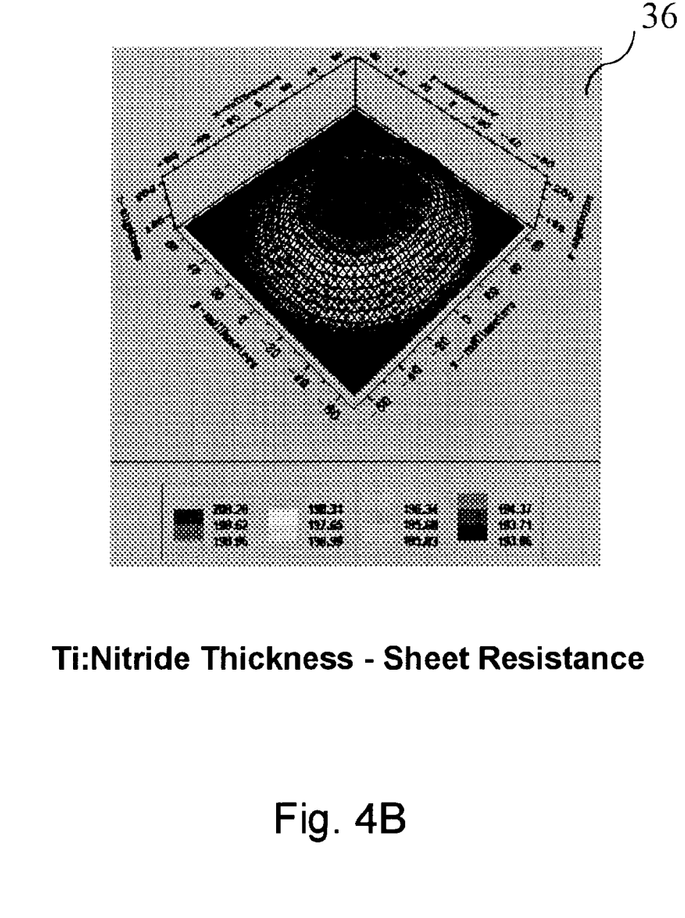

FIGS. 4A and 4B further indicate that film thickness as determined from signal amplitude can be used to determine film thickness. These figures show how a thickness contour map 35 measured by analyzing the amplitude of the signal waveform (FIG. 4A) compares favorably to a similar contour map 36 measured with a 4-point probe (FIG. 4B). The 4-point probe is well known in the art and measures film thickness by determining a "sheet resistivity" in a small (approximately 1 cm) area of the film. In both cases, the thickness contour maps were generated by determining thickness values at 81 sites distributed in a concentric circular pattern across the surface of the ti:nitride film. The 81 thickness values were then analyzed and plotted in a contour format. The thickness values shown in the legend of both figures have units of angstroms. Both contours indicate a domed thickness variation for the ti:nitride film. The similarity of the contours of these two maps indicates how the above-described method can accurately measure even small thickness changes across a surface of a thin ti:nitride film.

Figure 6:
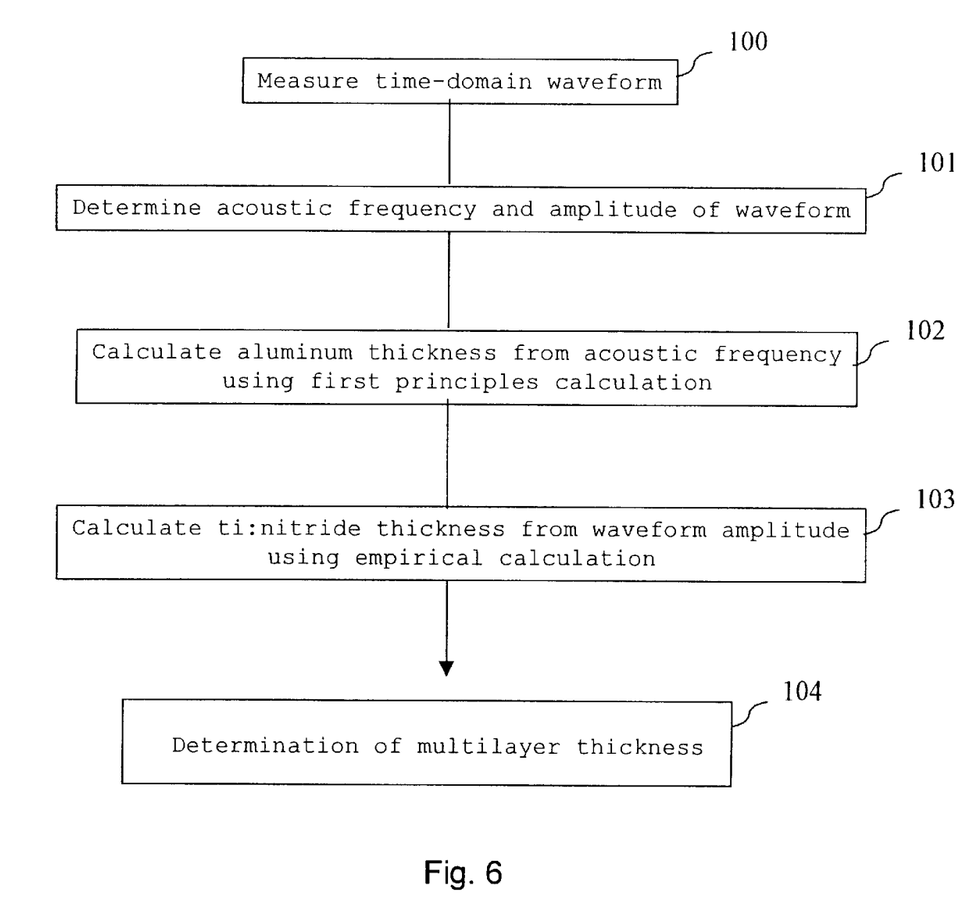
FIG. 6 is a flow chart describing a method for measuring multilayer thickness using ISTS.

Referring to FIG. 6, the film thickness values for a multilayer sample consisting of a ti:nitride film deposited on an aluminum film is determined by first measuring a time-domain signal waveform (step 100) similar to that shown in FIG. 1. The signal waveform features both a acoustic frequency and a signal amplitude. Once the signal waveform is measured, both its frequency and amplitude are determined (step 101). Acoustic frequency is typically determined by taking a fast Fourier transform of the singal waveform. This mathematical transform, well-known in the art, generates data indicating a signal amplitude as a function of frequency. The amplitude of the waveform can be determined simply by measuring the maximum value of the waveform. Alternatively, the amplitude can be determined by measuring the amplitude of the waveform at a specific point in time, or by fitting the waveform to a function that has an amplitude component.

As described above and indicated by the data in FIG. 5, the underlying aluminum thickness can be calculated from the acoustic frequency using a first principles calculation (step 102); this calculation is described in detail in pending and issued U.S. Patents referenced above. The ti:nitride thickness value is calculated from the waveform signal amplitude using an empirical calculation (step 103). For example, in this step a "look-up table" containing data that correlates signal amplitude to film thickness may be used for the empirical calculation. Such a look-up table would be determined, for example, using a set of known standard samples prior to making the ISTS measurement. In this case, the amplitude values in the look-up table should be determined in the same way that the amplitude is measured from the signal waveform. Alternatively, the look-up table could be generated using a mathematical calculation.

Once the acoustic frequency and signal amplitude are analyzed it is possible to determine the thickness of both the aluminum and ti:nitride layers (step 104).

Apparatus for Measuring the Thickness of Multiple Thin Films

Figure 7:
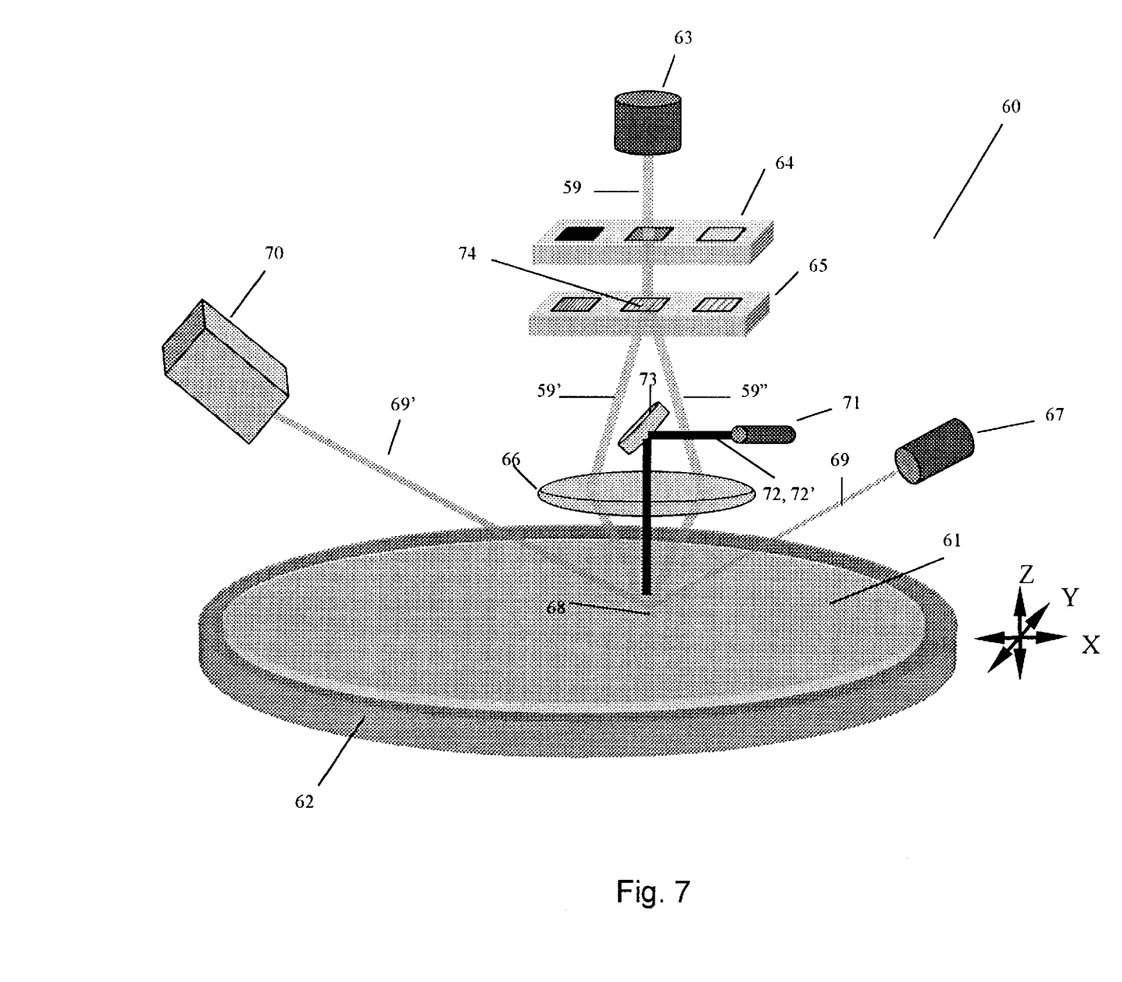
FIG. 7 is a schematic side view of an apparatus for simultaneously measuring at least two properties of a sample composed of multiple layers of films using ISTS.

Referring to FIG. 7, an optical system 60 measures at least two properties of a film structure 61 (e.g., a multilayer film structure) deposited on a substrate 62. Similar optical systems are described in pending and issued U.S. Pat. No. 5,633,711 (entitled MEASUREMENT OF MATERIAL PROPERTIES WITH OPTICALLY INDUCED PHONONS); U.S. Pat. No. 5,546,811 (entitled OPTICAL MEASUREMENT OF STRESS IN THIN FILM SAMPLES); and U.S. Pat. No. 5,812,261 (entitled METHOD AND DEVICE FOR MEASURING THE THICKNESS OF OPAQUE AND TRANSPARENT FILMS), the contents of which have been previously incorporated herein by reference.

In the system 60, an excitation laser 63 initiates time-dependent acoustic phonons in the thin film structure 61, and a second probe source 67 measures the response to generate a signal waveform similar to that shown in FIG. 1. The waveform is detected with a high-speed photodetector 70 and then analyzed to determine the property of interest.

The excitation laser 63 generates a pulse 59 that passes through neutral density filter 64 and a pattern 74 on diffracting phase mask 65. Phase masks are described, for example in issued U.S. Pat. No. 5,734,470 (entitled DEVICE AND METHOD FOR TIME-RESOLVED OPTICAL MEASUREMENTS), the contents of which are incorporated by reference. The phase mask pattern 74 separates pulse 59 into at least two excitation laser sub-pulses 59', 59". The pulses 59', 59" impinge an achromat lens pair 66 that focuses and overlaps them on the sample. There, the pulses optically interfere to form a spatially and temporally varying excitation pattern 68 on the surface of the film structure 61. The probe laser 67 measures acoustic waves initiated with the optical system 60 by generating a probe beam 69. The beam 69 features a pulse that impinges the structure's surface and is relatively long (typically 100 microseconds). A portion of probe beam 69 diffracts off of the acoustic phonons initiated by the excitation pattern 68 to form signal beam 69'. The photodetector 70 collects the signal beam 69' and generates a light-induced electronic signal. The signal is then analyzed with the data-acquisition electronics to generate a signal waveform which, in turn, determines a property of an underlying layer of the sample as described above.

Reflectivity measurements as described above are made with a small-scale reflectometer 71 positioned above the achromat lens pair 66. During operation, reflectometer 71 irradiates the surface of film 61 by reflecting a radiation beam 72 off a mirror 73 and through the achromat lens pair 66. The beam 72 is then focused on a measurement point near the excitation pattern 68. The beam 72 is reflected off of the sample surface, back through the achromat lens pair 66. There, the beam is reflected by mirror 73 into the reflectometer 71. The reflectometer 71 includes a detector and analyzer (not shown in the figure) that process the reflected beam 72' to determine a property (e.g., thickness) of the surface film of sample 61. Analysis of the reflected signal is done according to methods known in the art.

Other Embodiments

Figure 8:
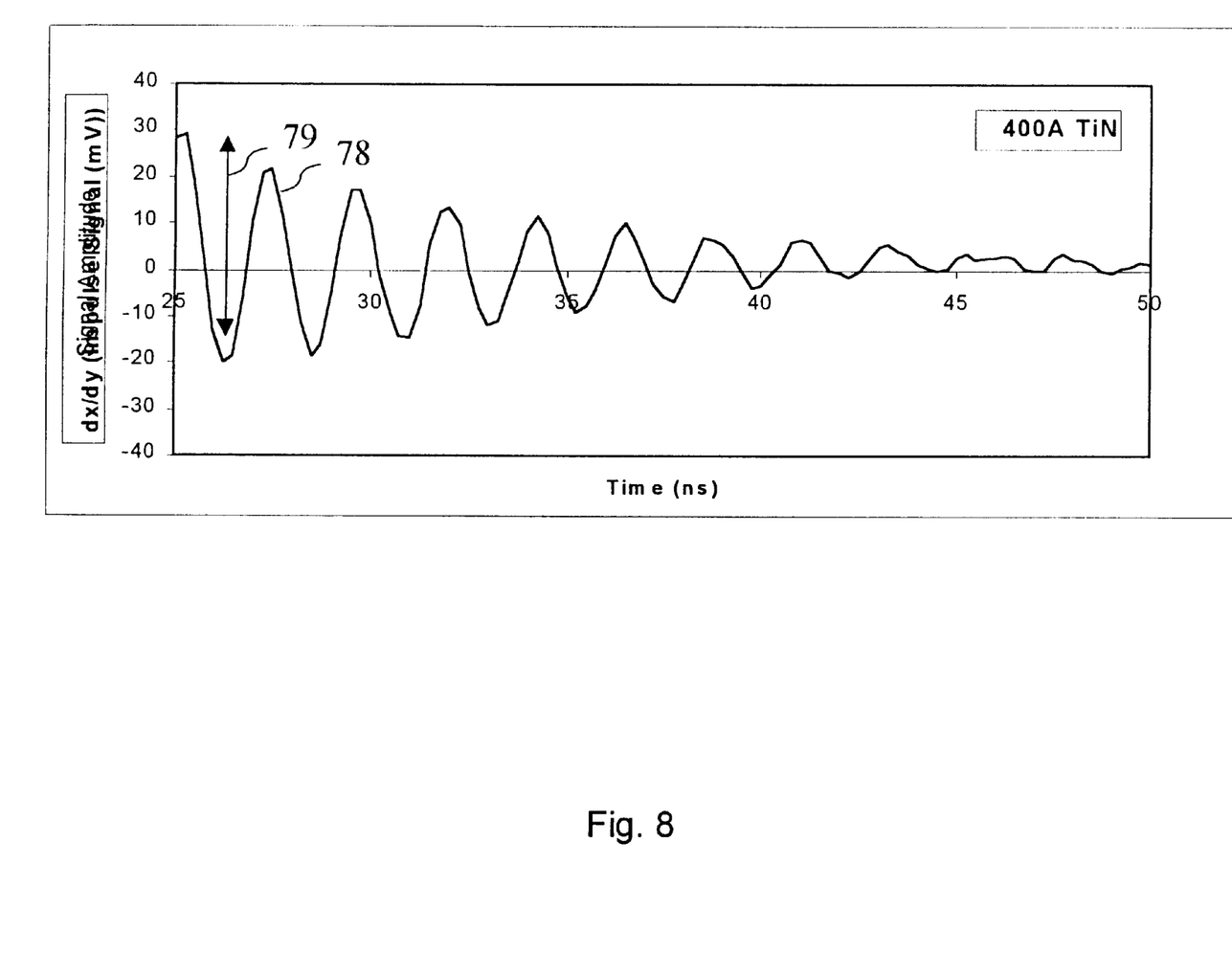
FIG. 8 is a graph showing the derivative of signal amplitude versus time measured from a 400-angstrom ti:nitride film deposited on an aluminum film.
Figures 9A, 9C:
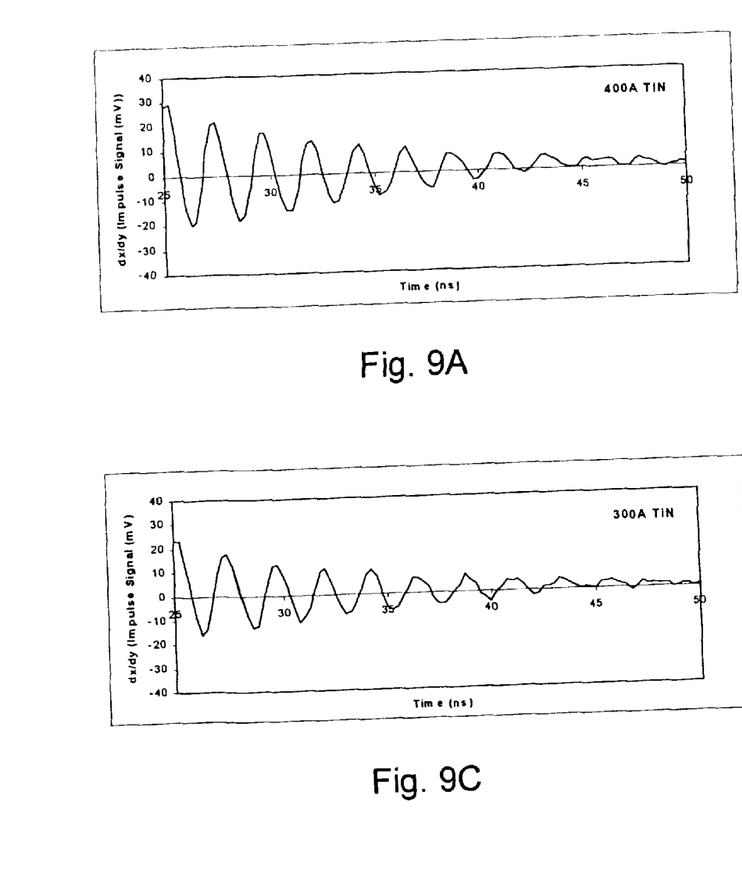
FIGS. 9A–9D are, respectively, graphs depicting the derivative of signal amplitude versus time of waveforms measured from samples of 400, 200, 300, and 100 angstroms of a ti:nitride film deposited on an aluminum film.
Figure 9B:
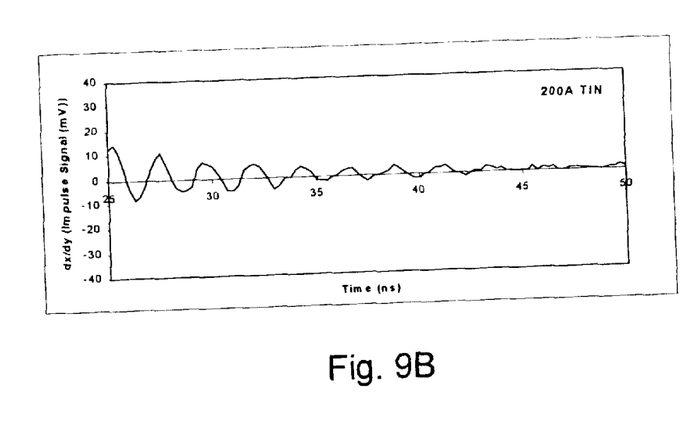
Figure 9D:
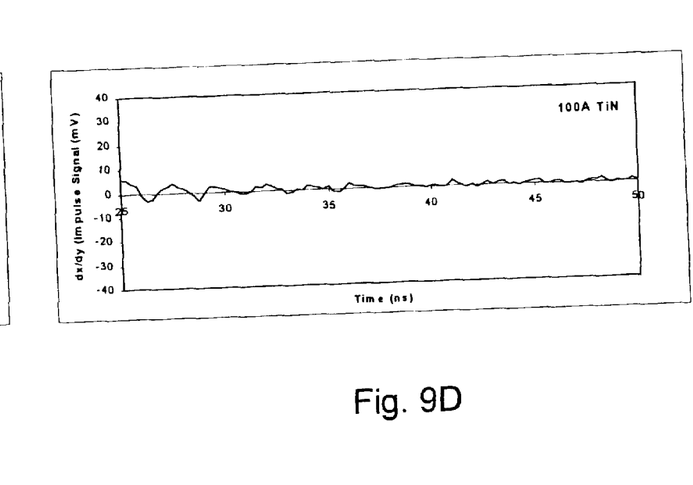

Other embodiments of the invention described above can also be used to simultaneously measure the thickness of multiple thin film deposited on a sample. Referring to FIG. 8, for example, a derivative waveform 78 of a signal waveform (similar, for example, to that shown in FIG. 1) can be generated and analyzed to determine the ti:nitride film thickness. To generate the derivative signal waveform, a signal waveform (similar to that shown in FIG. 1) was first measured from a ti:nitride/aluminum structure. The first derivative ($\delta y/\delta x$) of the signal waveform was then calculated and plotted for a portion of the waveform (in this case from 25 to 40 ns). Taking the derivative of the waveform effectively removes components of the waveform that vary with time on a slower scale than the acoustic oscillations (these are typically between 300 and 700 MHz). For example, taking the derivative of the waveform effectively removes from the signal waveform a slowly decaying exponential component attributed to thermal diffusion.

The depth of modulation (indicated by the arrow 79) of the derivative waveform 78, shown in the figure as the difference between the minimum and maximum of a first, single oscillation, is correlated to the thickness of the outer ti:nitride film. For example, to determine the thickness of the ti:nitride layer the depth of modulation 79 can be compared to a mathematical model that relates the depth of modulation to the thickness of the outermost layer of a multilayer sample. In this case, a look-up table, similar to that described above for use with signal amplitude, can be generated and used to determine film thickness.

FIGS. 9A–D show how depth of modulation varies with the thickness of an overlying ti:nitride film. These figures show derivative waveforms similar to that shown in FIG. 8 for samples featuring, respectively, 100, 200, 300, and 400 angstroms of ti:nitride deposited on 5000 angstroms of aluminum. As is clear from the graphs, the depth of modulation of the derivative waveform decreases as the ti:nitride film becomes thinner. Depth of modulation can therefore be used to calculate the ti:nitride film thickness using a look-up table, measured from a set of calibration samples as described above.

Figure 10:
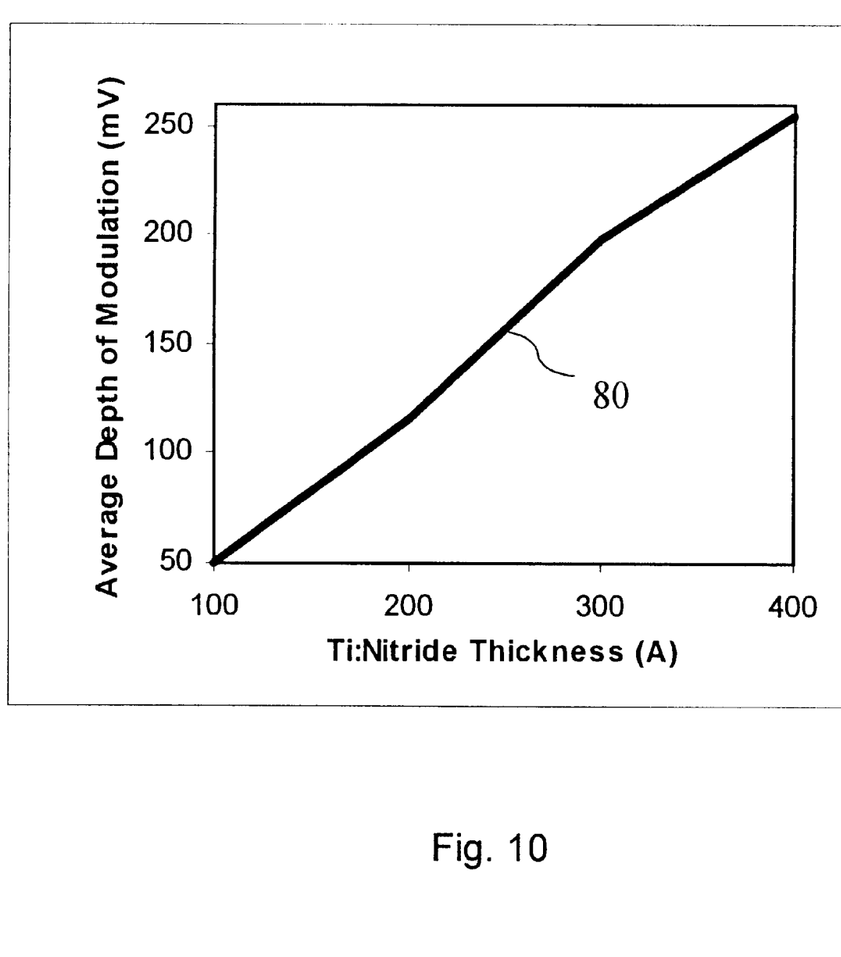
FIG. 10 is a graph showing the average depth of modulation versus ti:nitride thickness for the data shown in FIGS. 9A–9D.

FIG. 10 shows data 80 taken from FIGS. 9A–9D indicating how depth of modulation varies somewhat linearly with ti:nitride film thickness. In this case the depth of modulation is calculated from the average difference between the maximum and minimum values of each period in the oscillating derivative waveform. The dependence is somewhat linear, varying from about 50 mV for the 100 angstrom ti:nitride film to about 250 mV for the 400 angstrom ti:nitride film. The frequency of the acoustic oscillations (about 424.50 MHz) for the derivative waveforms in FIGS. 9A–9D is relatively constant and independent of the ti:nitride thickness. This value can be used to calculate the underlying aluminum thickness as described above.

Other methods can also be used to calculate the depth of modulation. For example, the derivative waveform could be fit to a function, f(x), such as $$f(x)=A_1\exp(-\gamma_1 x)\sin(\omega x \phi)$$

In this case function contains a sinusoidal oscillation that decays exponentially. In this function the decay constant $\gamma$; is proportional to the depth of modulation.

Still other embodiments are within the scope of the following claims.

What is claimed is:

1. A method for measuring properties of a sample comprising multiple layers of films comprising the steps of:
   a) irradiating a surface of the sample with at least one first source of excitation radiation to excite an acoustic mode within the sample;
   b) detecting the acoustic mode with a probe source of radiation to generate a first signal beam;
   c) irradiating a surface of the sample with at least one second source of radiation to generate a second signal beam which relates to reflection or absorption;
   d) analyzing the at least one first and at least one second signal beams to determine at least two properties of the sample.

2. The method of claim 1, wherein the second source or radiation reflects off of the sample to generate the second signal beam.

3. The method of claim 2, wherein the second signal beam differs from the second probe source of radiation in intensity, polarization, or a combination of intensity and polarization.

4. The method of claim 3, wherein the change in intensity, polarization, or combination of intensity and polarization is compared to a mathematical model to determine at least one additional property of the outermost layer of the sample.

5. The method of claim 4, wherein the at least one. property of the outermost layer of the sample is thickness.

6. The method of claim 5, wherein the at least one additional property of the outermost layer of the sample is density, roughness, composition, index of refraction, stoichiometry, refractive index, or absorption coefficient.

7. An apparatus for measuring properties of a sample comprising multiple layers of films comprising:
   at least one first source of probe radiation that irradiates the sample to generate a first signal beam;
   a detector for detecting the first signal beam;
   a second source of excitation radiation that irradiates the sample to generate a second signal beam;
   a detector for detecting the second signal beam which relates to reflection or absorption; and
   an analyzer to determine at least two properties of the sample from the at least one first and at least one second signal beams.

8. The apparatus of claim 7, wherein the analyzer further comprises a computer or microprocessor.

9. The apparatus of claim 8, wherein the second source of excitation radiation irradiates the surface of the sample and the radiation reflects off the surface to generate the second signal beam.

10. The apparatus of claim 9, wherein the analyzer measures a change in intensity between the second source of excitation radiation and the reflected second signal beam.

11. The apparatus of claim 10, wherein the computer or microprocessor compares the change in intensity between the second source of excitation radiation and the reflected second signal beam to a mathematical model to determine a property of the outermost layer of the. sample.

12. The apparatus of claim 11, wherein the property of the outermost layer of the sample is thickness.

13. The apparatus of claim 12, wherein the analyzer measures a change in polarization between the second source of excitation radiation and the reflected second signal beam.

14. The apparatus of claim 7, wherein the computer or microprocessor compares the change in polarization between the second source of excitation radiation and the reflected second signal beam to a mathematical model to determine the thickness of the outermost layer of the sample.

15. The apparatus of claim 14, wherein the property of the outermost layer of the sample is thickness, density, roughness, index of refraction, composition, absorption coefficient.

* * * * *